United States Patent [19]

Burris

[11] Patent Number: 5,082,558

[45] Date of Patent: Jan. 21, 1992

[54] COMPACT CONTACT LENS PURIFICATION SYSTEM USING OZONE GENERATOR

[76] Inventor: William A. Burris, 7 E. Jefferson Cir., Pittsford, N.Y. 14534

[21] Appl. No.: 575,622

[22] Filed: Aug. 31, 1990

[51] Int. Cl.⁵ .......................... A61L 2/20; A61F 9/00
[52] U.S. Cl. .................................. 210/167; 422/116; 422/119; 422/186.08; 422/186.1; 422/255; 422/300; 422/301; 422/305; 422/907; 55/158; 55/159; 134/102; 134/111; 134/138; 134/901; 206/5.1; 210/85; 210/139; 210/188; 210/192; 250/455.1
[58] Field of Search .............. 422/24, 29, 30, 105, 422/108, 110, 117, 119, 186.07, 186.08, 186.1, 292, 300, 305, 907, 301; 210/188, 192, 760, 85, 138, 143, 194, 195.1, 167, 136, 139; 55/159, 158; 261/DIG. 42; 206/5.1; 250/324, 455.1; 351/160 R; 134/109-111, 901, 102, 138

[56] References Cited

U.S. PATENT DOCUMENTS

| | | | |
|---|---|---|---|
| Re. 32,672 | 5/1988 | Huth et al. ............... | 252/95 |
| 3,692,180 | 9/1972 | LaRaus .................... | 210/192 |
| 3,726,404 | 4/1973 | Troglione ................ | 210/192 |
| 3,823,728 | 7/1974 | Burris ..................... | 210/760 |
| 3,873,696 | 3/1975 | Randeri ................... | 422/37 |
| 3,888,782 | 6/1975 | Boghosian et al. ....... | 252/106 |
| 3,910,296 | 10/1975 | Karageozian et al. ... | 134/2 |
| 3,954,965 | 5/1976 | Boghosian ............... | 424/81 |
| 4,029,817 | 6/1977 | Blanco et al. ............ | 424/80 |
| 4,098,964 | 7/1978 | Reber ...................... | 429/86 |
| 4,179,616 | 12/1979 | Coviello et al. .......... | 422/186.07 |
| 4,230,571 | 10/1980 | Dadd ....................... | 422/29 |
| 4,309,388 | 1/1982 | Tenney et al. ........... | 422/29 |
| 4,395,346 | 7/1983 | Kleist ...................... | 252/106 |
| 4,445,893 | 5/1984 | Bodicky ................... | 605/165 |
| 4,517,159 | 5/1985 | Karlson ................... | 422/20 |
| 4,599,166 | 7/1986 | Gesslauer ................. | 210/192 |
| 4,619,763 | 10/1986 | O'Brien ................... | 210/192 |
| 4,670,178 | 6/1987 | Huth et al. ............... | 252/106 |
| 4,703,761 | 11/1987 | Rathbone et al. ........ | 128/763 |
| 4,746,489 | 5/1988 | Arnold ..................... | 128/675 |
| 4,776,343 | 10/1988 | Hubbard et al. ......... | 210/192 |
| 4,842,723 | 6/1989 | Parks et al. .............. | 210/251 |

FOREIGN PATENT DOCUMENTS

| | | |
|---|---|---|
| 3440315 | 5/1986 | Fed. Rep. of Germany .............. 422/186.07 |
| 3722384 | 1/1989 | Fed. Rep. of Germany ......... 422/24 |
| 3830499 | 3/1990 | Fed. Rep. of Germany ....... 210/760 |

Primary Examiner—Robert A. Dawson
Assistant Examiner—Joseph Drodge
Attorney, Agent, or Firm—Eugene Stephens & Associates

[57] ABSTRACT

Contact lenses are purified by contact with ozone in a compact system that includes an ozone generator, a purifying liquid in a lens chamber, and a pumping system for flowing liquid and gas in a way that brings ozone dissolved in a purifying liquid into contact with the lenses. In some embodiments, undissolved ozone can also contact the lenses. Several preferred arrangements are shown for accomplishing the lens purification with such an ozone disinfection system.

56 Claims, 6 Drawing Sheets

COMPACT CONTACT LENS PURIFICATION SYSTEM USING OZONE GENERATOR

BACKGROUND

One of the biggest problems for wearers of contact lenses is the cleaning and disinfecting that these require. If dirt and microorganisms are not to enter the eye with the lenses, these must be cleaned, soaked, and disinfected using specified steps, materials, and treatment schedules for each type of contact lens. In spite of all the recommendations, lens wearers do suffer eye problems from poor lens hygiene, and it is well known that many lens wearers do not follow the suggested procedures faithfully enough to avoid eye problems from contact lenses introducing dirt and microorganisms into the eyes.

To help with the problem of contact lens hygiene, my invention applies ozone purification to the disinfecting of contact lenses. In doing so, I have focused on simple and effective systems that are inexpensive to manufacture and easy and convenient for a user to operate. My systems for purifying contact lenses facilitate the wearer's desire for simple and reliable lens disinfection, require minimum involvement by the wearer, and minimize chances of a failure. Achieving these goals with a small and inexpensive lens purifier is an intricate problem solved with varying degrees of sophistication by the several embodiments disclosed in this application. These embodiments use ozone for purifying the lenses, and they generate the ozone and apply it to the lenses in systems that represent approximately a 1000:1 reduction in scale from the present art of ozone purification.

SUMMARY OF THE INVENTION

My contact lens purification system brings a lens to be disinfected into contact with ozone, either dissolved in liquid or in a gaseous state, or both. The lens is held in a treatment chamber where the ozone contact occurs, while the lens is either submerged in or sprayed with a purifying liquid. A generator produces the ozone, and a pumping system that can include a gas pump, a liquid pump, or both, mixes the generated ozone with a purifying liquid and brings one or both into contact with the lens. My system also involves a compact device that can hold lenses in a convenient position for purification and can automatically operate the ozone generator and the pumping system for disinfecting the lenses. Appropriate purification can be timed and sensed, and any escape of ozone from the device can be made negligible.

DRAWINGS

All of the drawings are partially schematic diagrams of different preferred embodiments of my contact lens purification system. Each embodiment includes an ozone generator, a lens chamber where contact lenses can be purified, a pumping system for bringing ozone and a purifying liquid into contact, a reducer for diminishing the concentration of any escaping ozone, and a controller to ensure that lens purification occurs. The various embodiments of the drawings differ from each other in that:

DETAILED DESCRIPTION

Figure 1:
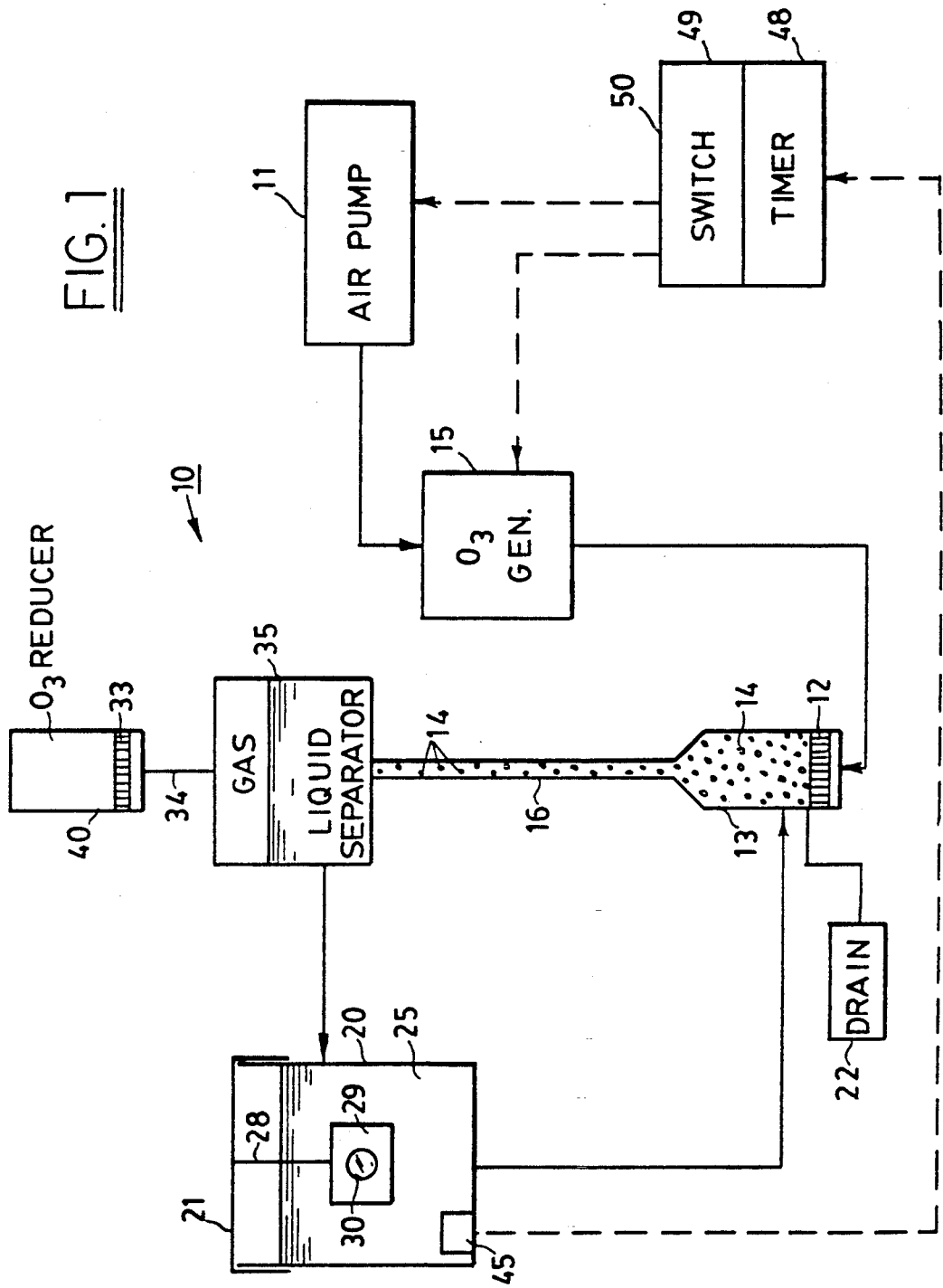
FIG. 1 shows a gas pump arranged for flowing an ozone containing gas through the ozone generator and for pumping purifying liquid in a circulation loop that includes a bubble line and a gas/liquid separator.

The preferred embodiments of the drawings have comparative advantages in features such as convenience, reliability, safety, cost, and compactness. Different embodiments, using different combinations of such features, may be preferred for different types of lenses or for users with different desires. The embodiments will be explained in the order presented in the drawings, but this does not imply any similar order of importance. Also, some of the different features that are illustrated in the drawings can be interchanged among the various embodiments, and the drawings are arranged to illustrate the different features that can be combined, and not to delimit one combination of features from another.

System 10 of FIG. 1 uses an air pump 11 as a prime mover, to cause the necessary gas and liquid flows to make the system work. Air pump 11 is preferably arranged upstream of ozone generator 13 so that it can force air through generator 15, which outputs a mixture of air and ozone. Pump 11 could be arranged downstream of ozone generator 15, except that an ozone environment is too corrosive and problematic for most pumps to handle.

The air and ozone mixture output from generator 15 is delivered to a diffuser 12 arranged at the entry to a chamber 13 that also receives purifying liquid 25 from lens chamber 20. Diffuser 12 is porous and allows gas to flow through, preferably in a way that divides the gas flow into a multitude of bubbles 14. Although air stones and other materials are available for diffuser 12, I prefer a porous, hydrophobic resin material that allows the air and ozone mixture to flow through, but resists any flow of liquid 25 in the opposite direction. Diffuser 12 can then serve as a liquid barrier ensuring that no purifying liquid 25 travels back to generator 15. This is important because the preferred form of generator 15 is a corona discharge device that would be damaged if liquid were to enter it.

Another way to ensure that liquid does not enter generator 15 is by directing the output from generator 15 to a level higher than the purifying liquid level within the system so that gravity prevents liquid from flowing through the elevated passageway to generator 15. This would require that the system not be turned over while it contains liquid 25 or that the elevated passageway includes a trap large enough to hold all the system liquid, if the system is turned over. A check valve can also be arranged in the output line from generator 15; and a check valve, like the porous hydrophobic resin material preferred for diffuser 12, can protect generator 15 from liquid 25, even if the system is overturned.

Purifying liquid 25 can be water or saline solution and can possibly contain other materials beneficial to the cleaning and disinfecting of lenses 30. These are arranged in a holder or container 29 that permits liquid 25 to contact lenses 30. Container 29 is mounted within lens chamber 20, preferably by an element 28 that suspends container 29 from cover 21. In the embodiment of FIG. 1, container 29 and lenses 30 are submerged under purifying liquid 25 in which ozone is dissolved so that flow of liquid 25 through chamber 20 contacts lenses 30 and purifies them by killing microorganisms and attacking other contaminants, as is generally known in the ozone purification art.

Although ambient air is a simple and preferred input for generator 15, it is also possible to use dried air that has passed through a dryer, to help keep moisture out of generator 15. Another possibility is supplying oxygen from a small container serving as the input to generator 15, which can produce more ozone from an oxygen supply than from an air supply.

A drain 22 is a convenient feature for system 10, so that purifying liquid 25 can be drained out whenever desired. This is especially important if system 10 is designed so that it should not be tilted for pouring liquid out of chamber 20. Also, it may be desirable in using purified liquid 25 for filling a lens storage case or for rinsing and cleaning out a lens holding case. For any of these purposes, drain 22 is preferably at the lowest liquid level within system 10, which in the illustration of FIG. 1 puts drain 22 at the bottom of chamber 13.

The amount of liquid 25 in system 10 is preferably predetermined, by the user pouring in the proper amount, for example. If saline solution is desired for liquid 25, this can be made within system 10 by adding a proper sized salt tablet to distilled water. Operation of system 10 purifies liquid 25, while purifying lenses 30, so that any contamination entering system 10 with a charge of liquid 25 can be purified by the ozone that circulates within system 10.

From chamber 13, where the air and ozone mixture from generator 15 is combined and contacted with purifying liquid 25 from chamber 20, a bubble line 16 extends to gas and liquid separator 35. Bubbles 14, rising in bubble line 16, make purifying liquid 25 flow with them from chamber 13 to separator 35. Bubble line 16 thus serves as a circulation pump for purifying liquid 25, under the motive power of air pump 11. Bubble line 16 then draws liquid 25 from chamber 20 into chamber 13, and on to separator 35 from which liquid flows back into chamber 20. In passing through chamber 13, bubble line 16, and separator 35, liquid 25 dissolves some ozone that enters chamber 20, to contact and purify lenses 30.

Air and any ozone that does not dissolve in liquid 25 within chamber 13, bubble line 16, and separator 35 are directed through vent 34 to an ozone reducer 40 that greatly reduces the concentration of ozone in gas escaping from separator 35. Reducer 40 contains at least one of several materials that are available for reducing ozone to oxygen so that raw ozone does not escape into the atmosphere. Even if raw ozone were to escape through vent 34, however, it should not present any health hazard in the small quantities used for operating system 10.

When reducer 40 is used and is filled with a catalytic or other material that reduces ozone to oxygen, it is important that purifying liquid 25 not reach the material within reducer 40, because liquid would impair its action. Working against this is the fact that bubbles 14 are entering separator 35 and bursting at the liquid surface there, creating spray droplets that can enter vent 34. Baffles are one possibility for keeping these spray droplets out of reducer 40, but baffles would not block liquid flow if the system were overturned. What I prefer, therefore, is a porous hydrophobic resin element 33 that allows gas, but not liquid, to enter reducer 40.

The system of FIG. 1 is preferably operated by a controller 50 that includes a switch 49 and a timer 48. The user preferably initiates a purifying cycle by operating switch 49, and the duration of the purifying process is controlled by timer 48. Starting up system 10 involves actuating air pump 11 and generator 15, and these should run for a long enough interval to purify lenses 30. It is desirable that system 10 run no longer than necessary for adequately purifying lenses 30, and the duration of operation can be controlled in several ways. A simple and preferred way is to set timer 48 for a predetermined interval so that once switch 49 is actuated, pump 11 and generator 15 operate for the timed interval before shutting off. This interval should be established to assure that liquid 25 is purified and lenses 30 are adequately contacted with ozone to ensure their purification. Depending on the ozone output rate of generator 15, two to ten minutes should suffice.

Sensor 45 can be arranged in lens chamber 25, or elsewhere in contact with liquid 25 containing dissolved ozone; and sensor 45 is placed in communication with control unit 50. Sensor 45 can detect a concentration of ozone in purifying liquid 25, and controller 50 can be made to act responsively to the ozone concentration information from sensor 45. Ozone purification involves both concentration of ozone and time of contact of lenses 30 with the ozone concentration. The more diluted the ozone concentration, the longer the time required for purification, and vice versa. By adding a simple microprocessor to controller 50, system 10 can be operated for a time interval suitable to the concentration of ozone in liquid 25 in chamber 20, as detected by sensor 45, to ensure that lenses 30 are appropriately disinfected when a purification cycle ends.

Sensor 45 can also be used in a more simple arrangement for merely verifying that ozone generator 15 is operating and delivering ozone to liquid 25 in lens chamber 20. For this, if sensor 45 does not detect ozone in liquid 25, a warning or indicator light could be illuminated to inform the operator that lenses 30 are not being purified.

Figure 2:
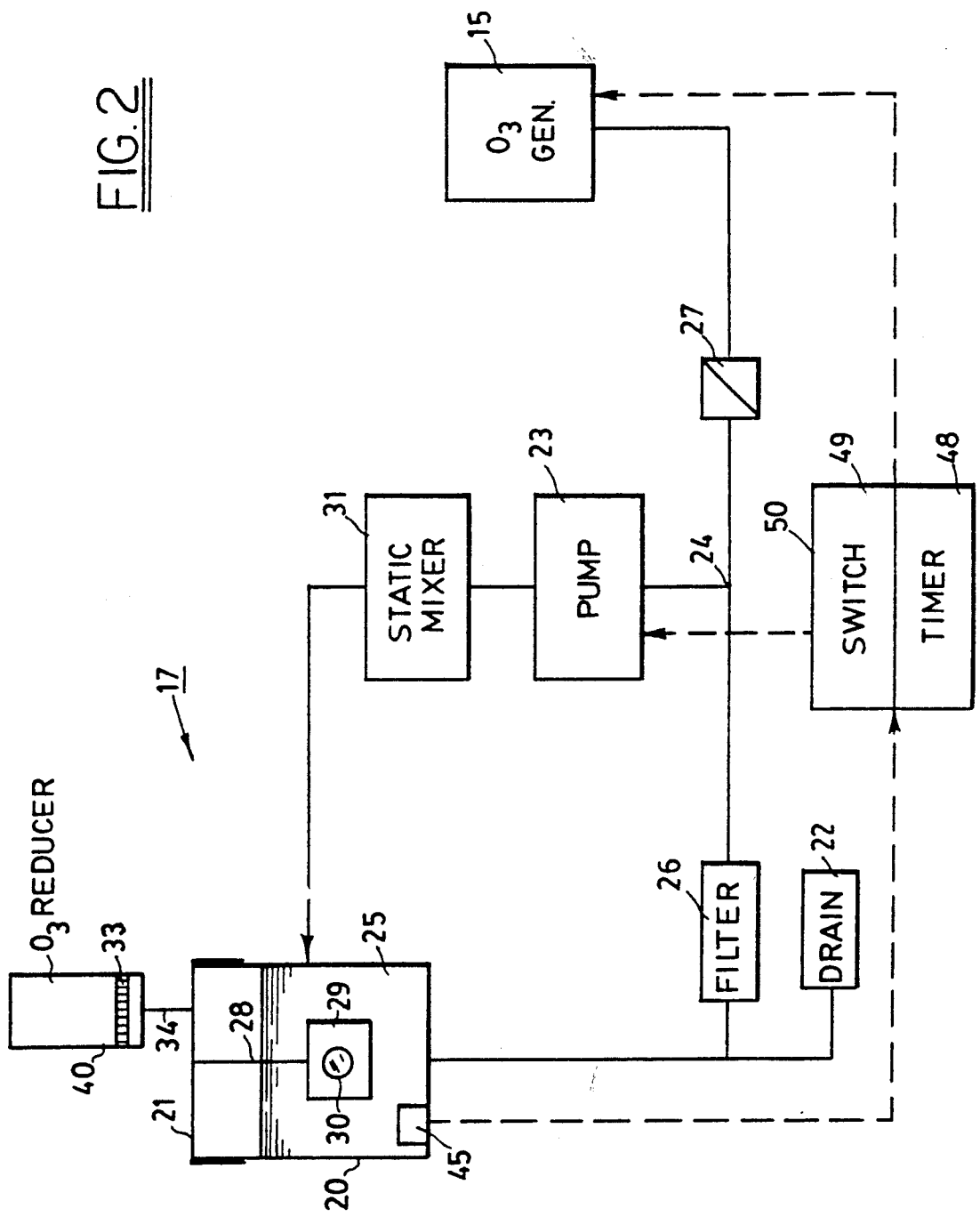
FIG. 2 shows a pump arranged for pumping both purifying liquid and an ozone containing gas through a circulation loop.

System 17 of FIG. 2 differs from system 10 primarily in the ways that venting, pumping, and liquid and gas flows occur. Venting is through the cover 21 of lens chamber 20, instead of from a gas and liquid separator, but otherwise venting preferably includes vent 34, porous hydrophobic element 33, and reducer 40 that reduces the concentration of any ozone escaping to atmosphere.

The prime mover for flow in system 17 is pump 23, arranged for pumping both purifying liquid 25 and a gas mixture that includes ozone, which flows from generator 15 and combines with liquid 25 at a T 24. Pump 23 is preferably a positive displacement pump, such as a gear pump, which helps mix and contact together the ozone mixture and the purifying liquid. The piping of these materials to pump 23 is sized to proportion the respective flows for combining ozone with the liquid at a desirable rate and for providing an adequate circulational flow through lens chamber 20 to ensure that lenses 30 are contacted by ozone dissolved in purifying liquid 25. The circulational flow can also be arranged for directing liquid flow over the surfaces of lenses 30 at a rate that is adequate for removing dirt particles from lenses 30, which can thus be cleaned by the combined effects of ozone purification and agitational contact with liquid.

A filter 26 can be arranged in the line between lens chamber 20 and junction 24, but filter 26 can also be omitted. Ozone contact may precipitate some materials from purifying liquid 25, depending on its purity when introduced into the system; and impurities may be removed from lenses 30, from the agitation action of the ozone and the purifying liquid 25 that flows over lenses 30. Either impurity can be captured by filter 26. Also, a desirable drain 22 for system 17 can allow liquid 25 to be changed frequently enough so that filtration may not be necessary.

A check valve 27 is shown in the line between ozone generator 15 and T junction 24, to ensure that liquid 25 does not enter generator 15. Other alternatives, as previously explained, can include elevating the output line from generator 15 to a level above liquid 25 or using a porous hydrophobic element to block liquid back flow.

A static mixer 31 is shown downstream of pump 23, to ensure thorough mixing of the liquid and gas before these reach lens chamber 20. Mixer 31 can be eliminated whenever pump 23 itself provides adequate mixing. Static mixer 31 can also be arranged downstream of the gas and liquid contact region in other embodiments where additional liquid and gas mixing is desirable.

The control of system 17 can be similar to the control described for system 10. Also, the separator 35, with its ozone reducer 40, can be incorporated into system 17, rather than venting gas through chamber cover 21.

Figure 3:
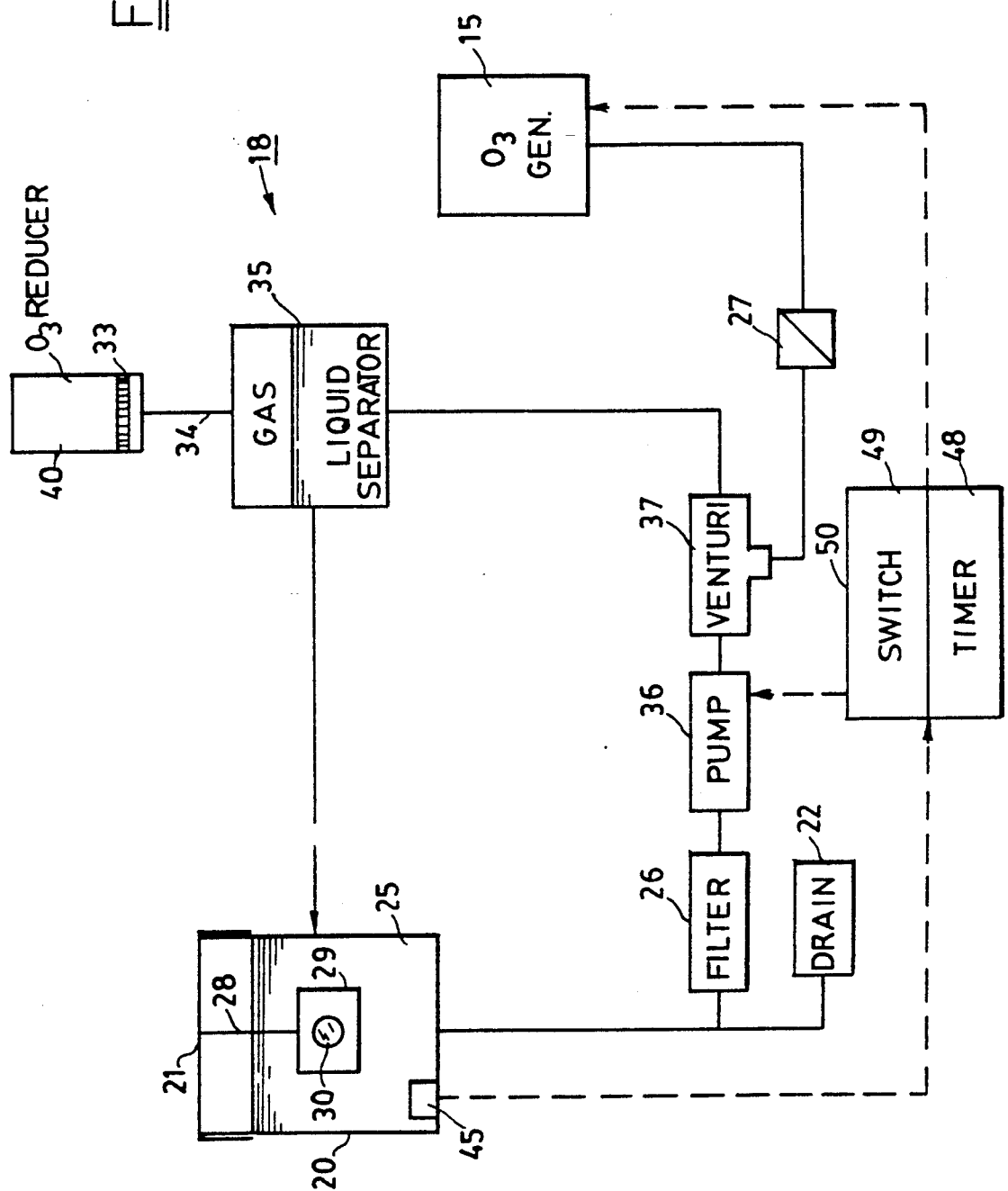
FIG. 3 shows a liquid pump arranged for forcing liquid through a venturi where it is combined with an ozone containing gas in a circulation loop that includes a gas/liquid separator.

System 18 of FIG. 3 is similar to system 10, except for the pumping and combining of the liquid and gas. Liquid pump 36 pumps liquid from lens chamber 20 through venturi 37 where an air and ozone mixture from generator 15 is entrained with the flowing liquid. Purifying liquid 25 can flow through filter 26 enroute to pump 36, if desired, and a check valve 27 or other restriction against liquid backflow can be arranged in the output line from ozone generator 15. Venturi 37 is sized to entrain the ozone gas mixture at . flow rate that is appropriate to the liquid output flow from pump 36. Venturi 37 also contacts the liquid and gas phases together and helps mix these two to facilitate dissolving ozone within the liquid. A static mixer 31, such as shown in system 17 of FIG. 2, can be arranged downstream of venturi 37, if necessary, to ensure adequate mixing of gas and liquid.

System 18 can use a similar control 50, gas and liquid separator 35, ozone reducer 40, lens container 29, and drain 22 as previously described for systems 10 and 17. The liquid level shown in gas and liquid separator 35 can be controlled by gravity and by proper dimensioning of flow lines, as explained for system 10, or a float valve can be arranged to control liquid level in separator 35. In fact, a float valve liquid level control is also possible for separator 35 in system 10, and for liquid level control purposes in other illustrated embodiments.

Figure 4:
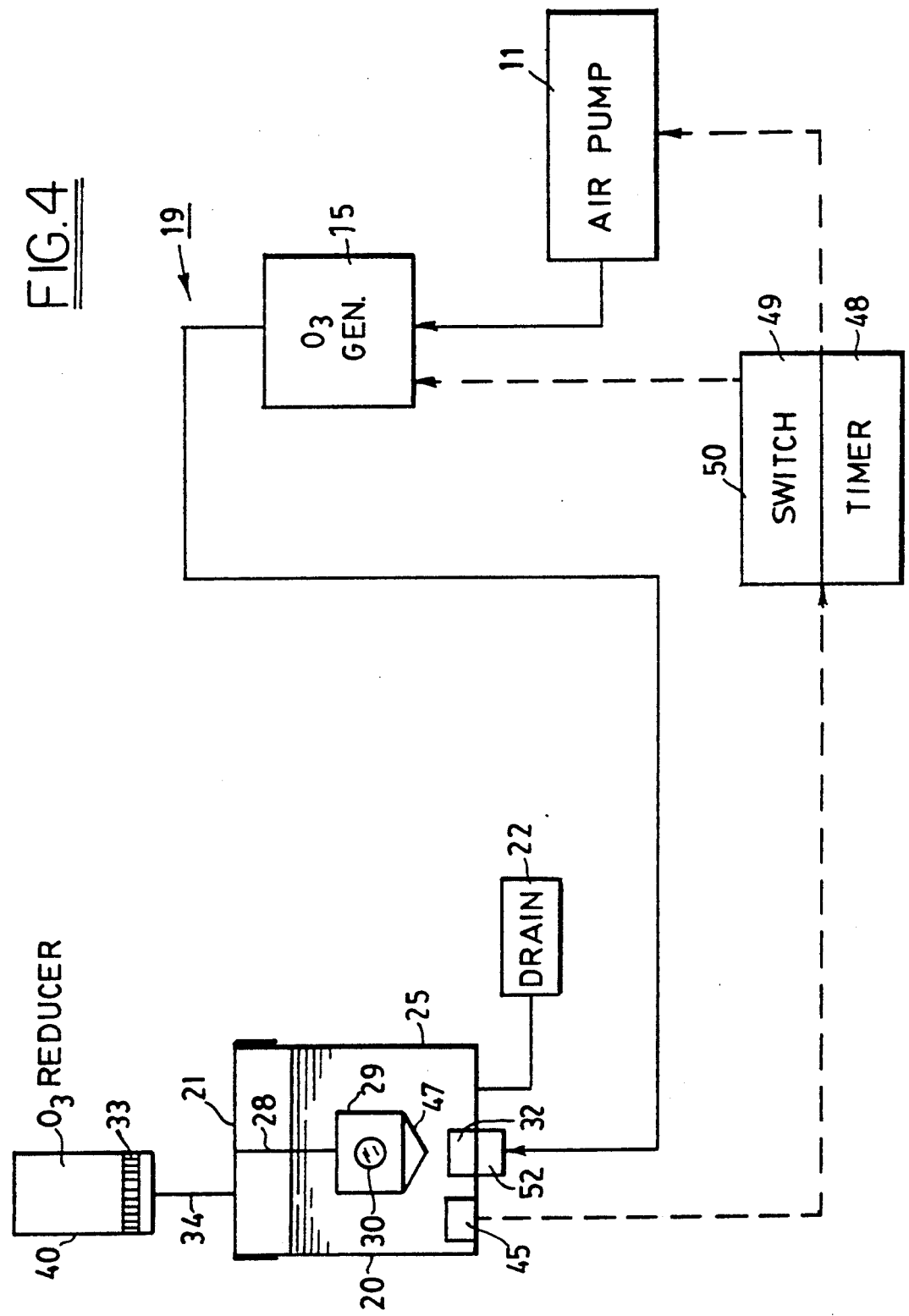
FIG. 4 shows a gas pump arranged for forcing an ozone containing gas through an ozone generator and directly into a lens chamber where lenses are contacted by both gaseous and dissolved ozone.

The embodiment 19 of FIG. 4, instead of using a liquid flow loop bypassing lens chamber 20, directly bubbles an air and ozone mixture from generator 15 into purifying liquid 25 in lens chamber 20. This can contact lenses 30 in holder 29 directly with some gaseous ozone, as bubbles rise through liquid 25 in chamber 20. Lenses 30 must be able to tolerate direct contact with ozone for this operation to be satisfactory.

Alternatively, a baffle 47 can divert the rising ozone bubbles around lens 30 so that there is no direct contact of lens 30 with ozone bubbles. Either way, some of the ozone in the rising bubbles also dissolves in purifying liquid 25, and dissolved ozone in liquid 25 also contacts lenses 30 for purification purposes. Also, the rising bubbles of ozone can drive a circulational flow of liquid 25 in chamber 20 so that moving liquid carrying dissolved ozone contacts lenses 30. For this purpose, ozone bubbles preferably rise in the vicinity of lenses 30 even if they are baffled out of contact with lenses 30. Ozone bubbles can also provide agitation at the surfaces of lenses 30, for dislodging dirt particles on the lenses; and providing the lenses can withstand direct contact with ozone, baffle 47 can be arranged for directing ozone bubbles to flow against the surfaces of lenses 30 to accomplish agitational cleaning along with ozone purification.

The output line leading from ozone generator 15 to lens chamber 20 preferably rises above the level of liquid 25 in chamber 20 so that liquid 25 cannot flow from chamber 20 back to ozone generator 15, so long as system 19 stays upright. A diffuser 32 arranged at the gaseous entrance to chamber 20 divides the gas flow into bubbles that rise through and dissolve in purifying liquid 25, which contacts lenses 30 in holder 29. Diffuser 32 is preferably formed of a porous hydrophobic resin material that not only allows the gas mixture to pass freely into purifying liquid 25, but also serves to block the flow of liquid 25 back toward generator 15, even if the system is overturned.

A vent 34 from chamber 20 preferably includes an ozone reducer 40, as previously explained. The only pump required for embodiment 19 is air pump 11, which forces air or oxygen through generator 15 and forces the ozone gas mixture output from generator 15 into chamber 20 via diffuser 32. Control 50 can be arranged in any of the previously described ways.

Chamber 20 can be made disconnectable from ozone generator 15, preferably by a quick-connecting and disconnecting junction 52 where the line from ozone generator 15 delivers its gaseous output to diffuser 32. This can allow chamber 20 to serve as a portable holder for lenses 30 and to be plugged back into the rest of system 19 whenever desirable for purifying lenses 30.

While chamber 20 is disconnected from the rest of system 19, the preferred hydrophobic nature of diffuser 32 can prevent liquid 25 from leaking out of chamber 20 via the gas input; and the preferred hydrophobic element 33, in ozone reducer 40, can prevent liquid 25 from leaking out of chamber 20 via ozone reducer 40. Chamber 20, with or without ozone reducer 40, is preferably made compact, for portability, and is also preferably made to cooperate with the rest of system 19 simply by being replugged into connection 52. If a sensor 45 is arranged in chamber 20, this is preferably automatically reconnected with controller 50 whenever chamber 20 is plugged back into system 19. The disconnection of chamber 20 so that it can be portable, apart from the rest of system 19, can also be applied to the other illustrated embodiments, which can be provided with the necessary disconnectable connections.

Figure 5:
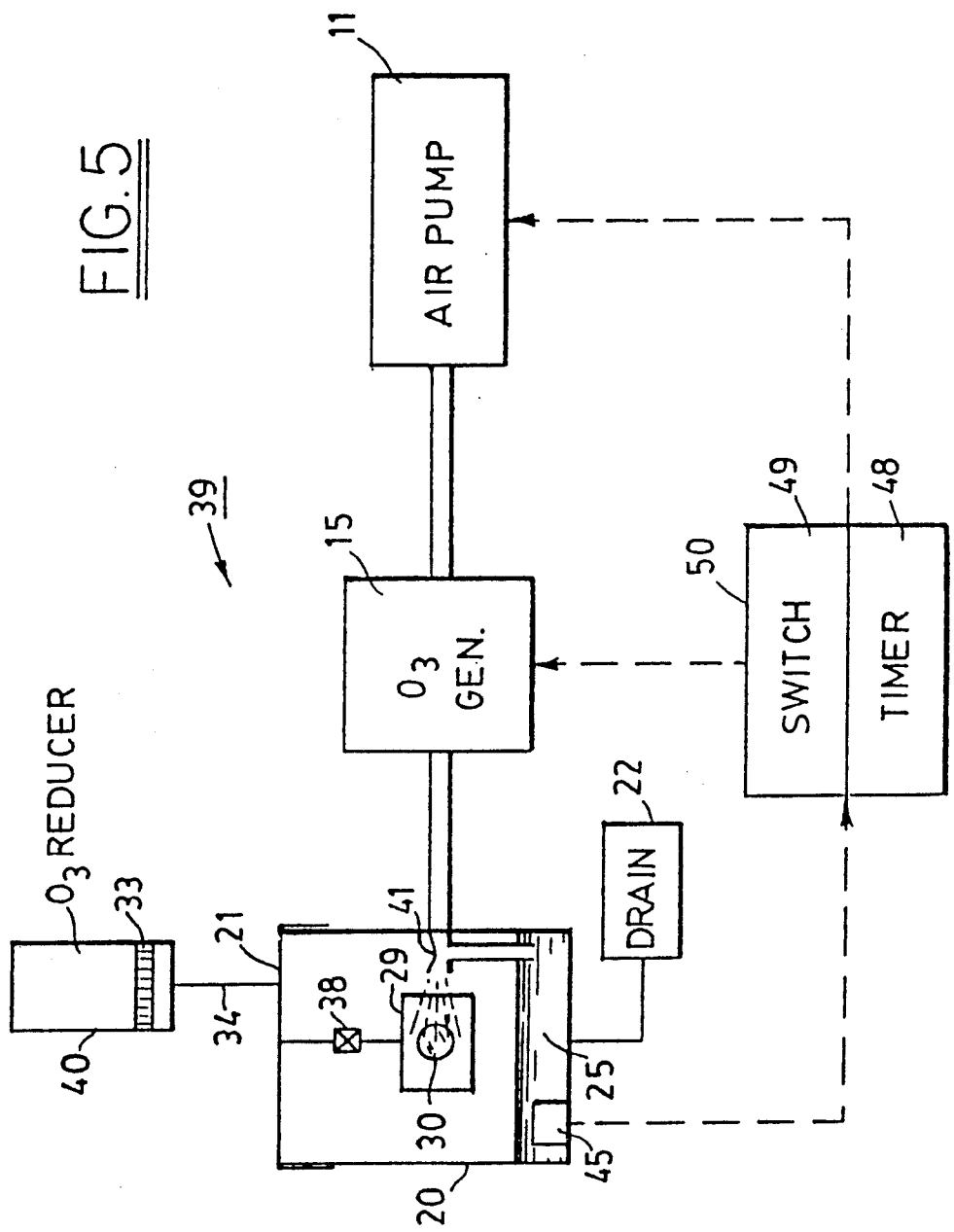
FIG. 5 shows a gas pump arranged for forcing an ozone containing gas through an ozone generator and through a venturi spray nozzle that combines ozone with a purifying liquid sprayed onto contact lenses.

Embodiment 39 of FIG. 5 directs a spray of purifying liquid 25 and a gas mixture including ozone against lenses 30 in holder 29 within lens chamber 20. This is caused by air pump 11 forcing air through generator 15 and forcing an output mixture of air and ozone through venturi 41, which draws up and entrains purifying liquid 25. The output from venturi 41 is a spray of liquid and gas directed against lenses 30.

Liquid 25 includes dissolved ozone, but some undissolved ozone also contacts lenses 30, which must be able to withstand this. Liquid spray drops contacting and passing by lenses 30 fall into a reservoir of liquid 25 that collects at the bottom of lens chamber 20. The liquid spray also provides a vigorous agitational contact of liquid drops against the surfaces of lenses 30, to dislodge and remove dirt particles.

A bearing 38 can be arranged to allow lens holder 29 to rotate freely so that the spray from venturi 41 can rotate holder 29 and direct a spray against all exposed surfaces of lenses 30. To accomplish this, the spray from venturi 41 is directed off the axis of the support provided for holder 29 by bearing 38. This can set lenses 30 whirling within their holder 29 while the surfaces of lenses 30 are bombarded with liquid spray drops, to purify the lenses with ozone while knocking loose and removing dirt particles. Venting from chamber 20 is preferably arranged through ozone reducer 40, and system 39 can be operated by controller 50, both as previously described.

Figure 6:
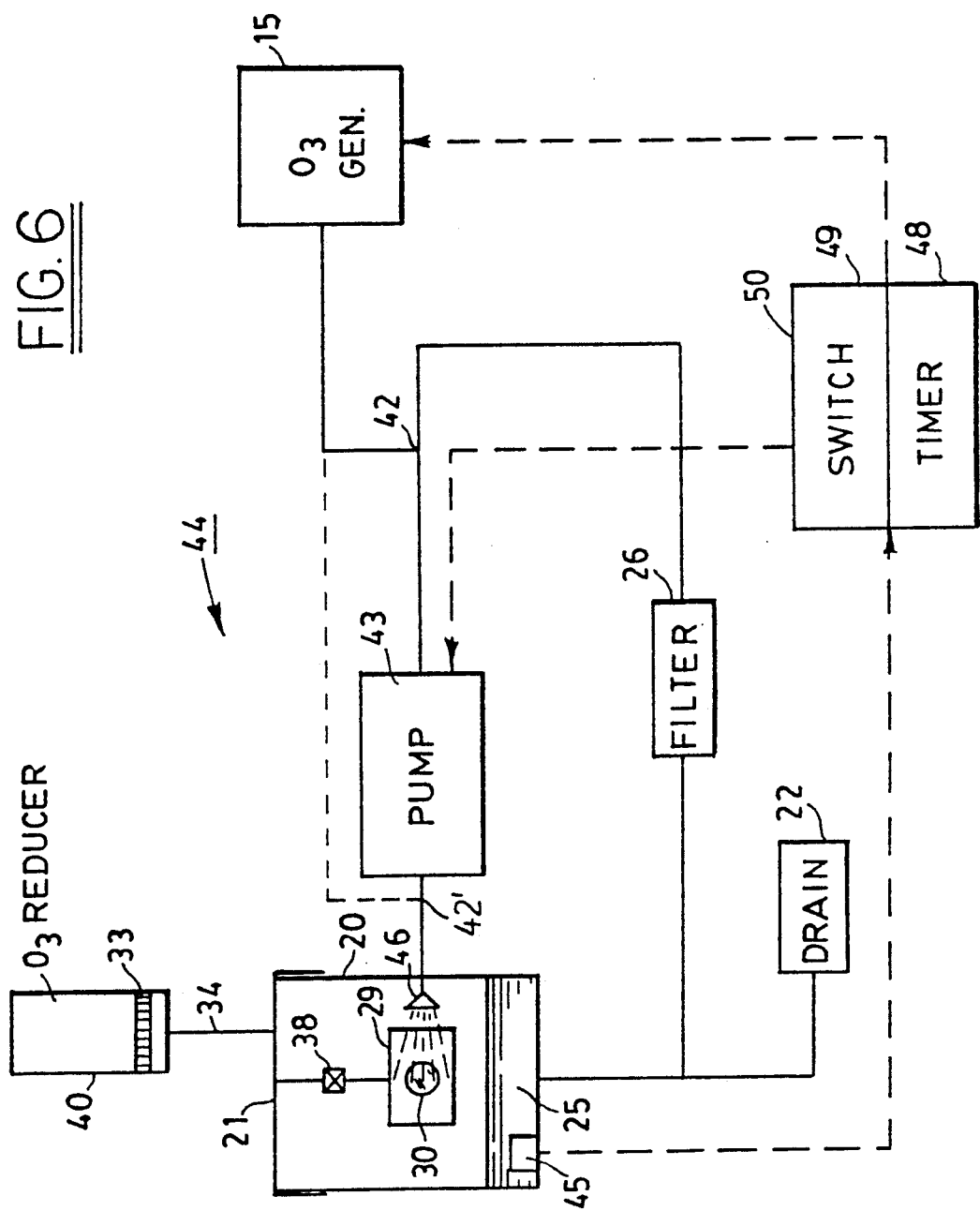
FIG. 6 shows a liquid pump arranged for forcing a mixture of a purifying liquid and an ozone containing gas entrained with the liquid through a nozzle directing a spray onto contact lenses.

System 44 of FIG. 6, like system 39 of FIG. 5, also directs a spray of air and ozone mixed with purifying liquid against lenses 30 and holder 29, which is also preferably made free to rotate by bearing 38. Instead of an air pump powering a spray nozzle, however, liquid pump 43 forces purifying liquid 25 through a bypass loop that can include a filter 26 and does include a T 42 where an ozone gas mixture from generator 15 is entrained in the flow of liquid 25. The gaseous and liquid mixture is forced by pump 43 through spray nozzle 46, which directs a purifying spray against lenses 30. The liquid output from pump 43 can produce a vigorous spray that can remove dirt from lenses 30 by agitation, while the spray drops also purify lenses 30 with the ozone they contain. T 42 can be moved downstream of pump 43 to the 42' position at the end of the broken line extension of the output line from generator 15.

Ozone becomes dissolved in purifying liquid 25, which collects in a reservoir at the bottom of lens chamber 20. Gas vented from chamber 20 preferably passes through ozone reducer 40, and controller 50 operates the system as previously explained. A gas and liquid separator 35, such as illustrated in the embodiments of FIGS. 1 and 3, can be arranged in system 44, between T 42 or 42' and nozzle 46 so that lenses 30 are sprayed only with liquid containing dissolved ozone, and not directly with undissolved ozone gas.

I claim:

1. A contact lens purification system comprising:
   a. a chamber containing a contact lens submerged in a liquid configured and arranged for purification system;
   b. a generator arranged for producing an ozone containing gas;
   c. a liquid circulation passageway arranged for leading said liquid from said chamber to a junction;
   d. an output gas passageway leading said ozone containing gas from said generator to said junction;
   e. said liquid circulation passageway being arranged for leading said liquid from said junction back to said chamber;
   f. a pumping system arranged for causing said liquid to flow through said liquid circulation passageway and causing said ozone containing gas to contact said liquid at said junction for dissolving ozone in said liquid in regions downstream of said junction; and
   g. said liquid and gas passageways and said pumping system being sized to determine the flows of said liquid and said ozone containing gas.

2. The purification system of claim 1 wherein said pumping system includes a pump arranged downstream of said junction so that said pump mixes said ozone containing gas and said liquid.

3. The purification system of claim 1 wherein said junction comprises a venturi arranged downstream from a pump in said liquid passageway so that liquid pumped through said venturi draws said ozone containing gas from said generator through said gas passageway and into said venturi.

4. The purification system of claim 1 wherein said pumping system includes a gas pump arranged for pumping said ozone containing gas to said junction, and a bubble line extends upward from said junction for pumping said liquid and said ozone containing gas.

5. The purification system of claim 1 including a contact chamber in said liquid circulation passageway downstream of said junction where said ozone containing gas is bubbled through said liquid.

6. The purification system of claim 1 including a porous diffuser arranged in said gas passageway at said junction for dividing said ozone containing gas into bubbles contacting said liquid.

7. The purification system of claim 1 including a porous hydrophobic element arranged in said gas passageway to act as a check valve preventing said liquid from entering said generator.

8. The purification system of claim 1 including means for preventing said liquid from entering said generator.

9. The purification system of claim 1 including means for separating said liquid from said ozone containing gas after said contact.

10. The purification system of claim 1 including means for reducing the escape of ozone to atmosphere.

11. The purification system of claim 10 including means for preventing said liquid from entering said escape reducing means.

12. The purification system of claim 10 wherein said escape reducing means includes a vent arranged for venting ozone containing gas only through a material that reduces the ozone concentration in the vented gas.

13. The purification system of claim 1 including a filter arranged in said liquid passageway.

14. The purification system of claim 1 including a timer arranged for determining a duration of operation of said system.

15. The purification system of claim 1 including a sensor arranged for sensing a concentration of ozone in said liquid.

16. The purification system of claim 1 wherein said liquid passageway includes a static mixer arranged downstream of said junction for increasing contact between said liquid and said ozone containing gas.

17. The purification system of claim 1 including a drain arranged for draining said liquid from said system.

18. The purification system of claim 1 wherein said pumping system is arranged for flowing said liquid past said contact lens for removing dirt from said lens.

19. A contact lens purification system comprising:
   a. a chamber configured and arranged for containing a contact lens submerged beneath a surface of a liquid;
   b. a generator arranged for producing an ozone containing gas;
   c. a pump arranged for pumping said ozone containing gas from said generator into said liquid in said chamber; and
   d. a porous hydrophobic diffuser arranged beneath the surface of said liquid in said chamber to cover an inlet for said ozone containing gas flowing into said chamber so that said ozone containing gas passes through said diffuser into said liquid in said chamber, and liquid in said chamber cannot pass through said diffuser toward said generator.

20. The purification system of claim 19 including means for reducing the escape of ozone to the atmosphere.

21. The purification system of claim 20 including means for preventing liquid from entering said escape reducing means.

22. The purification system of claim 21 wherein said liquid preventing means includes a porous hydrophobic element arranged between said liquid and said escape reducing means.

23. The purification system of claim 20 wherein said escape reducing means includes a closure for said chamber and a vent arranged for venting ozone containing gas only through a material that reduces the ozone concentration in the vented gas.

24. The purification system of claim 19 including a timer arranged for determining a duration of operation of said system.

25. The purification system of claim 19 including an ozone sensor arranged for sensing a concentration of ozone in said liquid in said chamber.

26. The purification system of claim 19 including a drain arranged for draining said liquid from said chamber.

27. The purification system of claim 19 including means for disconnecting said chamber and said diffuser from said generator.

28. The purification system of claim 19 including means for directing said ozone containing gas into agitational contact with surfaces of said lens, for removing dirt from said lens.

29. a contact lens purification system comprising:
   a. a chamber configured and arranged for containing a contact lens submerged in a liquid;
   b. a generator arranged for an ozone containing gas;
   c. a pump arranged for pumping said ozone containing gas from said generator into said liquid in said chamber;
   d. means for preventing liquid from entering said generator; and
   e. means for reducing the escape of ozone into the atmosphere.

30. The purification system of claim 29 wherein said means for preventing liquid from entering said generator includes a porous hydrophobic material arranged between said generator and said chamber in a passageway for said ozone containing gas.

31. The purification system of claim 29 wherein said means for reducing the escape of ozone into the atmosphere includes a closure for said chamber and a vent arranged for venting ozone containing gas only through a material that reduces the ozone concentration in the vented gas.

32. The purification system of claim 29 including means for preventing liquid from entering said escape reducing means.

33. The purification system of claim 32 wherein said liquid preventing means includes a porous hydrophobic element.

34. The purification system of claim 29 including a diffuser arranged for dividing said ozone containing gas into bubbles contacting said liquid.

35. The purification system of claim 34 wherein said diffuser is arranged for directing said bubbles to cause said liquid to flow past said contact lens.

36. The purification system of claim 29 including a timer arranged for determining a duration of operation of said system.

37. The purification system of claim 29 including an ozone sensor arranged for sensing a concentration of ozone in said liquid.

38. The purification system of claim 29 including means for disconnecting said chamber from said generator.

39. The purification system of claim 38 including means for preventing liquid from escaping from said chamber through said disconnecting means.

40. The purification system of claim 39 wherein said liquid escape preventing means is a porous hydrophobic material.

41. A contact lens purification system comprising:
   a. a chamber configured and arranged for containing a contact lens;
   b. a generator arranged for producing an ozone containing gas;
   c. a liquid containing reservoir; and
   d. a pumping system arranged for causing said ozone containing gas to contact said liquid and to dissolve ozone in said liquid and for causing said liquid and said dissolved ozone to be sprayed on said contact lens.

42. The purification system of claim 41 wherein said pumping system includes a gas pump for flowing said ozone containing gas, and a liquid pump for spraying said liquid and said dissolved ozone on said contact lens.

43. The purification system of claim 41 wherein said pumping system includes a pump arranged for flowing both said liquid and said ozone containing gas in mutual contact before being sprayed on said contact lens.

44. The purification system of claim 41 wherein said pumping system includes a gas pump for flowing said ozone containing gas from said generator through a venturi which draws said liquid from said reservoir and contacts said liquid with said ozone containing gas before spraying said contact lens.

45. The purification system of claim 41 including means for draining said liquid from said chamber into said liquid reservoir so that said liquid is recirculated through said pumping system.

46. The purification system of claim 41 wherein a lower portion of said chamber serves as said liquid reservoir so that said liquid is recirculated through said pumping system.

47. The purification system of claim 41 including means for reducing the escape of ozone to the atmosphere.

48. The purification system of claim 47 including means for preventing liquid from entering said means for reducing the escape of ozone to the atmosphere.

49. The purification system of claim 48 wherein said liquid preventing means includes a porous hydrophobic element.

50. The purification system of claim 47 wherein said escape reducing means includes enclosing said system and venting ozone containing gas only through materials that reduce the ozone concentration in the vented gas.

51. The purification system of claim 41 including a filter arranged in a passageway for said liquid.

52. The purification system of claim 41 including means for preventing liquid from entering said generator.

53. The purification system of claim 41 including a timer for determining a duration of operation of said system.

54. The purification system of claim 41 including an ozone sensor arranged for sensing a concentration of ozone in said liquid.

55. The purification system of claim 41 including means for moving said lens while said lens is being sprayed by said liquid and said dissolved ozone.

56. The purification system of claim 55 wherein said lens is arranged in a holder mounted so that said spraying turns said holder.

* * * * *

UNITED STATES PATENT AND TRADEMARK OFFICE
CERTIFICATE OF CORRECTION

PATENT NO. : 5,082,558

DATED : January 21, 1992

INVENTOR(S) : William A. Burris

It is certified that error appears in the above-identified patent and that said Letters Patent is hereby corrected as shown below:

Col. 7, claim 1, line 60, after chamber, insert --configured and arranged for--; lines 61 and 62, delete "configured and arranged for purification system".

Signed and Sealed this

Twelfth Day of April, 1994

Attest:

BRUCE LEHMAN

Attesting Officer

Commissioner of Patents and Trademarks